United States Patent

Kiesele et al.

[11] Patent Number: 6,024,853
[45] Date of Patent: Feb. 15, 2000

[54] ELECTROCHEMICAL OXYGEN SENSOR

[75] Inventors: Herbert Kiesele; Frank Mett, both of Lübeck, Germany

[73] Assignee: Drägerwerk AG, Lubeck, Germany

[21] Appl. No.: 09/275,180

[22] Filed: Mar. 24, 1999

Related U.S. Application Data

[63] Continuation of application No. 08/982,107, Dec. 1, 1997, abandoned.

[30] Foreign Application Priority Data

Jun. 21, 1997 [DE] Germany ............................ 197 26 453

[51] Int. Cl.[7] .................................................. G01N 27/404
[52] U.S. Cl. ......................... 204/412; 204/402; 204/415; 204/431; 205/783
[58] Field of Search .................................... 204/402, 415, 204/431, 432, 412; 205/782.5, 783, 782

[56] References Cited

U.S. PATENT DOCUMENTS

| | | | |
|---|---|---|---|
| 3,328,277 | 6/1967 | Solomons et al. | 204/415 |
| 3,503,861 | 3/1970 | Volpe | 204/415 |
| 3,526,577 | 9/1970 | Molloy | 204/415 |
| 4,152,233 | 5/1979 | Chand | 204/415 |
| 4,187,162 | 2/1980 | Dageforde | 204/415 |
| 4,227,974 | 10/1980 | Petesen et al | 204/415 |
| 4,435,268 | 3/1984 | Martin et al. | 204/415 |
| 5,403,463 | 4/1995 | Braden et al | 204/431 |
| 5,547,554 | 8/1996 | Kiesele | 204/415 |
| 5,855,750 | 1/1999 | Kiesele | 204/415 |

FOREIGN PATENT DOCUMENTS

| | | |
|---|---|---|
| 31 20 159 A1 | 12/1982 | Germany . |
| 0 496 527 A1 | 7/1992 | Germany . |
| 0 620 433 A2 | 10/1994 | Germany . |
| 0 620 433 A3 | 10/1994 | Germany . |
| 4231256 | 12/1995 | Germany . |

*Primary Examiner*—T. Tung
*Attorney, Agent, or Firm*—McGlew and Tuttle, P.C.

[57] ABSTRACT

An electrochemical oxygen sensor with a measuring electrode, an atmospheric oxygen electrode as a reference electrode, and an auxiliary electrode in an electrolyte is improved such that a stable measured signal is obtained even during changes in the position of the measuring cell. To accomplish this, the auxiliary electrode is arranged in the vicinity of the measuring electrode and a protective electrode is provided between the measuring electrode and the auxiliary electrode.

20 Claims, 2 Drawing Sheets

ELECTROCHEMICAL OXYGEN SENSOR

This is a continuation of application Ser. No. 08/982,107 filed Dec. 1, 1997, now abandoned and the entire disclosure of this prior application is considered to be part of the disclosure of the accompanying application and is hereby incorporated by reference therein.

FIELD OF THE INVENTION

The present invention pertains to an electrochemical oxygen sensor with a measuring electrode, a noble metal/air electrode as a reference electrode and an auxiliary electrode in an electrolyte.

BACKGROUND OF THE INVENTION

An electrochemical oxygen sensor with a noble metal/air electrode as a reference electrode has been known from DE 42 31 256 C2. This oxygen sensor operates according to the principle of the "oxygen pump" and has a very long service life, because no sacrificial anode is consumed, as it is known from galvanic measuring cells. Oxygen is released at an auxiliary electrode, which is frequently also called a counterelectrode. The oxygen released at the auxiliary electrode may interfere with both the reference electrode and the measuring electrode. The interaction with the measuring electrode is especially disturbing, because excessively high oxygen contents may be mimicked. The auxiliary electrode is therefore arranged away from the measuring electrode, namely, behind the reference electrode, in the prior-art oxygen sensor.

However, it has been found that this measure alone is not sufficient, because if the oxygen sensor is moved, e.g., in portable measuring devices, electrolyte solution rich in oxygen, due to the change in position suddenly reaches the measuring and reference electrodes and thus it directly or indirectly causes a change in the electrode signal. In addition, the resistance of the electrolyte between the electrodes changes during the movement of the oxygen sensor, because the sensor is usually filled with electrolyte only partially, which may lead to potential variations especially at the measuring electrode.

SUMMARY AND OBJECTS OF THE INVENTION

The primary object of the present invention is to improve an electrochemical measuring cell of the above-mentioned type such that a stable measured signal is obtained even in the case of changes in position.

According to the invention, an electrochemical oxygen sensor is provided with a measuring electrode, a noble metal/air electrode as a reference electrode and an auxiliary electrode in an electrolyte. The auxiliary electrode is arranged in the vicinity of the measuring electrode and a protective electrode is provided between the measuring electrode and the auxiliary electrode.

The advantage of the present invention is essentially that the oxygen-producing auxiliary electrode is no longer arranged behind the reference electrode, but between the measuring electrode and the reference electrode and that a protective electrode, which is used to shield the measuring electrode from the auxiliary electrode, is provided between the measuring electrode and the auxiliary electrode. The protective electrode and the auxiliary electrode are located directly behind the measuring electrode. A nearly constant oxygen concentration profile develops behind the measuring electrode in this arrangement of the electrodes, and this concentration profile displays hardly any changes even during the movement of the sensor. Furthermore, the resistance of the electrolyte can be substantially reduced due to the short distance between the measuring electrode and the auxiliary electrode.

Separators in the form of thin, hydrophilic mats, with which a defined distance can be set between the electrodes in an especially simple manner, are advantageously present between the measuring electrode, the protective electrode and the auxiliary electrode.

An especially advantageous shielding of the measuring electrode against the auxiliary electrode is achieved, in addition to the protective electrode, by a protective electrode ring arranged around the measuring electrode, with which the radial diffusion of oxygen to the measuring electrode is prevented. The protective electrode covers both the measuring electrode and the protective electrode ring. The more the measuring electrode is covered by the protective electrode, i.e., the larger the cross-sectional area of the protective electrode compared with the measuring electrode, the better is the shielding of the measuring electrode against the radial diffusion of oxygen from the electrolyte space.

Another improvement in the shielding of the auxiliary electrode against the measuring electrode is achieved if the protective electrode is moved especially close to the measuring electrode or to the measuring electrode and the protective electrode ring. Distances between about 50 $\mu$m and 2 mm proved to be especially advantageous.

The various features of the novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
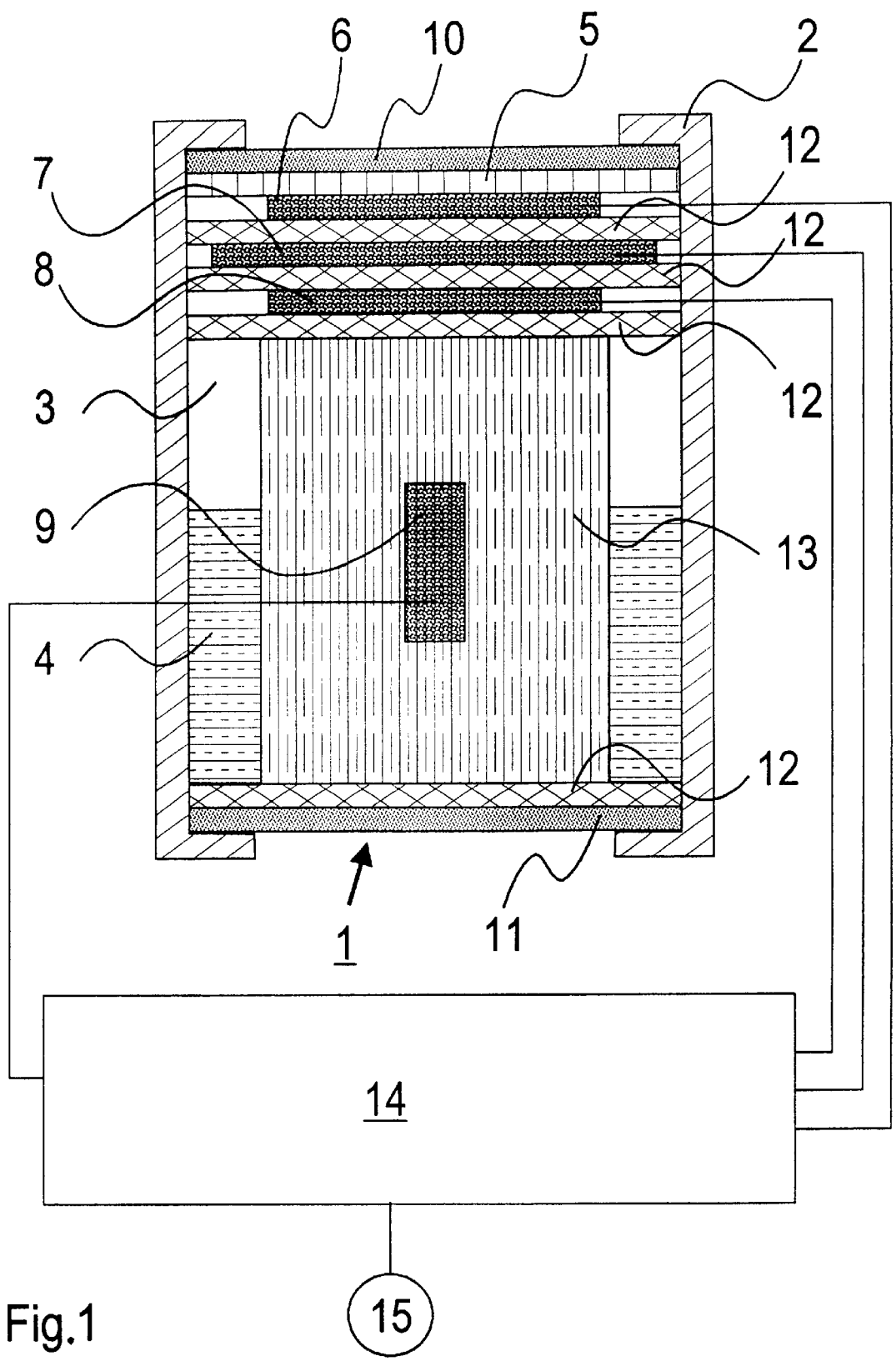
FIG. 1 is a schematic cross sectional view of a first embodiment of an electrochemical sensor according to the invention.

FIG. 1 schematically shows a sensor housing 2 of an electrochemical sensor 1 for detecting oxygen in a gas mixture. The sensor housing 2 encloses an electrolyte space 3 for accommodating an electrolyte 4 suitable for the oxygen measurement, e.g., sulfuric acid. A measuring electrode 6, a protective electrode 7, an auxiliary electrode 8, and a reference electrode 9 are arranged in the electrolyte space 3 behind a PTFE diffusion membrane 5. The diffusion membrane 5, which has a thickness of up to 50 $\mu$m, is held in the sensor housing 2 by a porous support membrane 10. The rear side of the sensor housing 2 is closed with a porous PTFE disk 11, through which the oxygen is equalized with the environment. The sensor housing 2 also consists of porous PTFE in order to improve the exchange of oxygen with the environment and to guarantee a position-independent pressure equalization. The distance between the electrodes 6, 7, 8 is set by means of thin, electrolyte-impregnated mats 12.

Another mat 12 between the auxiliary electrode 8 and a porous glass body 13 accommodating the reference electrode 9 ensures a position-independent contact of the electrolyte. The reference electrode 9 is arranged at a widely spaced location from the auxiliary electrode 8. As is shown in the drawings, the distance between the reference electrode and the auxiliary electrode is greater than the distance between the auxiliary electrode and the protective electrode or even the measuring electrode. As is also shown in the drawings, the cross sectional area of the protective electrode is larger than the cross sectional area of the measuring electrode.

The measuring electrode 6, the protective electrode 7, the auxiliary electrode 8, and the reference electrode 9 are made of the same material. Gold and platinum as well as their alloys and doped, platinum-coated carbon are especially suitable. The current generated by the oxygen to be detected at the measuring electrode is processed in an evaluating unit 14, which is connected to the electrodes 6, 7, 8, 9, into a measured signal representative of the oxygen concentration, and is displayed on a display unit 15. The evaluating unit 14 contains a potentiostat, not shown in the figure, with which the potential of the protective electrode 7 is set to that of the measuring electrode 6.

Figure 2:
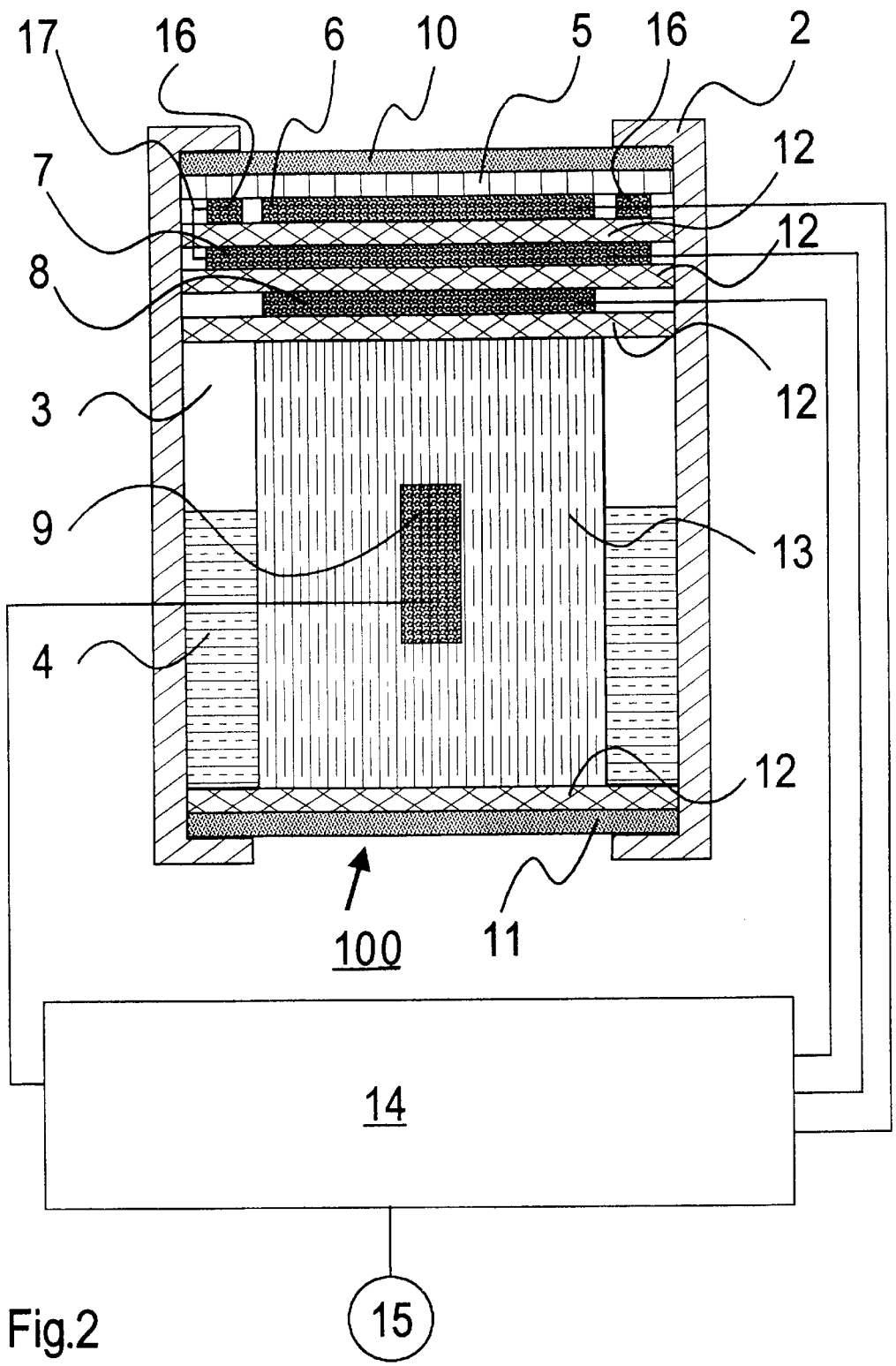
FIG. 2 is a schematic cross sectional view of a second embodiment of an electrochemical sensor according to the invention.

FIG. 2 shows an alternative embodiment of an electrochemical sensor 100, in which a protective electrode ring 16 is arranged around the measuring electrode 6, unlike in the case of the sensor 1 according to FIG. 1, in order to prevent the radial diffusion of oxygen from the electrolyte space 3 toward the measuring electrode 6. The protective electrode ring 16 is connected in terms of potential to the protective electrode 7 via a line 17.

While specific embodiments of the invention have been shown and described in detail to illustrate the application of the principles of the invention, it will be understood that the invention may be embodied otherwise without departing from such principles.

What is claimed is:

1. An electrochemical oxygen sensor based on an oxygen pump principal with electrodes of non sacrificial material, the sensor comprising:

a measuring electrode;

a noble metal/air electrode as a reference electrode;

an electrolyte;

an oxygen releasing auxiliary electrode in said electrolyte, said auxiliary electrode being arranged in a vicinity of said measuring electrode;

a protective electrode between said measuring electrode and said auxiliary electrode; and an evaluating unit connected to said reference electrode, connected to said auxiliary electrode, connected to said protective electrode and connected to said measuring electrode for detecting current generated by oxygen to be detected at the measuring electrode and forming a measuring signal representative of an oxygen concentration of the oxygen to be detected based on an oxygen pump principle.

2. The sensor in accordance with claim 1, wherein:

said auxiliary electrode is arranged between said reference electrode and said protective electrode.

3. The electrochemical oxygen sensor in accordance with claim 1, further comprising:

an electrolyte-impregnated separator adjacent said measuring electrode and said protective electrode, and another electrolyte-impregnated separator adjacent said auxiliary electrode and said protective electrode;

said evaluating unit is electrically connected to said electrodes to cause said auxiliary electrode to generate oxygen.

4. The electrochemical oxygen sensor in accordance with claim 3, wherein:

said separator between said measuring electrode and said protective electrode has a thickness between about 50 $\mu$m and 2 mm.

5. The electrochemical oxygen sensor in accordance with claim 1, wherein;

a potential of said protective electrode is set to a potential of said measuring electrode.

6. The electrochemical oxygen sensor in accordance with claim 1, further comprising:

a protective electrode ring surrounding a peripheral surface of said measuring electrode.

7. The electrochemical oxygen sensor in accordance with claim 6, wherein:

said protective electrode ring is electrically connected to said protective electrode.

8. The sensor in accordance with claim 1, wherein:

a cross sectional area of said protective electrode is larger than a cross sectional area of said measuring electrode.

9. The sensor in accordance with claim 1, wherein:

a distance between said reference electrode and said auxiliary electrode is greater than a distance between said auxiliary electrode and said measuring electrode.

10. The sensor in accordance with claim 1, wherein:

a distance between said reference electrode and said auxiliary electrode is greater than a distance between said auxiliary electrode and said protective electrode.

11. An electrochemical oxygen sensor using an oxygen pump principal, the sensor comprising:

a sensor housing defining an electrolyte space and an opening communicating said electrolyte space with an exterior of said housing;

electrolyte arranged in said electrolyte space;

a diffusion membrane positioned across said opening and blocking movement of said electrolyte through said opening, said membrane passing oxygen from the exterior of said housing to said electrolyte space;

a noble metal/air electrode forming a reference electrode and arranged in said electrolyte space;

a measuring electrode arranged in said electrolyte space between said reference electrode and said membrane;

a protective electrode arranged between said reference electrode and said measuring electrode;

an auxiliary electrode arranged between said reference electrode and said protective electrode; and an evaluating unit connected to said reference electrode, connected to said auxiliary electrode, connected to said protective electrode and connected to said measuring electrode for detecting current generated by oxygen passing through said membrane and forming a measuring signal representative of an oxygen concentration of the oxygen based on an oxygen pump principle, said evaluating unit being electrically connected to said electrodes to cause said auxiliary electrode to generate oxygen, said electrodes being formed of a material and said evaluating unit operating said electrodes to prevent said material of said electrodes from being consumed during detecting of oxygen.

12. The sensor in accordance with claim 11, further comprising:

a first separator arranged adjacent said measuring electrode and said protective electrode;

a second separator arranged adjacent said protective electrode and said auxiliary electrode.

13. The sensor in accordance with claim 12, wherein:

a cross sectional area of said protective electrode is larger than a cross sectional area of said measuring electrode;

a distance between said reference electrode and said auxiliary electrode is greater than a distance between said auxiliary electrode and said measuring electrode;

a protective electrode ring radially surrounds said measuring electrode, wherein said protective electrode ring is electrically connected to said protective electrode;

said evaluating unit operates said protective electrode to shield said measuring electrode from said oxygen produced by said auxiliary electrode.

14. The sensor in accordance with claim 11, wherein:

a cross sectional area of said protective electrode is larger than a cross sectional area of said measuring electrode.

15. The sensor in accordance with claim 11, wherein:

a distance between said reference electrode and said auxiliary electrode is greater than a distance between said auxiliary electrode and said measuring electrode.

16. The sensor in accordance with claim 11, wherein:

a distance between said reference electrode and said auxiliary electrode is greater than a distance between said auxiliary electrode and said protective electrode.

17. The sensor in accordance with claim 11, further comprising:

a protective electrode ring radially surrounding said measuring electrode, wherein said protective electrode ring is electrically connected to said protective electrode.

18. An electrochemical oxygen sensor, comprising:

a sensor housing made of a porous material for oxygen exchange with the environment and for position independent pressure equalization, said sensor housing defining an electrolyte space;

an electrolyte partially filling said electrolyte space;

a diffusion membrane;

a porous support membrane holding said diffusion membrane in said sensor housing adjacent to a sensor housing first end;

a measuring electrode disposed adjacent to said diffusion membrane;

a porous body disposed within said sensor housing electrolyte space;

a noble metal/air electrode forming a reference electrode, said reference electrode being accommodated in said porous body to provide said reference electrode with sensor housing position independent contact with said electrolyte;

an auxiliary electrode disposed in said electrolyte, said auxiliary electrode being arranged between said reference electrode and said measuring electrode;

a protective electrode disposed between said measuring electrode and said auxiliary electrode;

an electrolyte-impregnated separator disposed adjacent said measuring electrode and said protective electrode;

an electrolyte-impregnated separator disposed adjacent said auxiliary electrode and said protective electrode; and an evaluating unit connected to said reference electrode, connected to said auxiliary electrode, connected to said protective electrode and connected to said measuring electrode for detecting current generated by oxygen to be detected at the measuring electrode and forming a measuring signal representative of an oxygen concentration of the oxygen to be detected based on an oxygen pump principle, said evaluating unit being electrically connected to said electrodes to cause said auxiliary electrode to generate oxygen, said electrodes being formed of a material and said evaluating unit operating said electrodes to prevent said material of said electrodes from being consumed during detecting of oxygen.

19. The electrochemical oxygen sensor in accordance with claim 18, wherein:

said evaluating unit includes a potential for setting the potential of said protective electrode to that of said measuring electrode; said evaluating unit operating said protective electrode to shield said measuring electrode from said oxygen produced by said auxiliary electrode.

20. The electrochemical oxygen sensor in accordance with claim 18, further comprising:

a protective electrode ring wherein said measuring electrode is substantially radially surrounded by said protective electrode ring, wherein said protective electrode ring is connected to said protective electrode.

* * * * *